US012690946B1

(12) United States Patent
Fraher

(10) Patent No.: US 12,690,946 B1
(45) Date of Patent: Jul. 28, 2026

(54) SYRINGE AND RELATED METHODS

(71) Applicant: Thomas Fraher, Wilmington, CA (US)

(72) Inventor: Thomas Fraher, Wilmington, CA (US)

( * ) Notice: Subject to any disclaimer, the term of this patent is extended or adjusted under 35 U.S.C. 154(b) by 0 days.

(21) Appl. No.: 19/333,665

(22) Filed: Sep. 19, 2025

(51) Int. Cl.
| | |
|---|---|
| *A61C 1/08* | (2006.01) |
| *A61C 17/028* | (2006.01) |
| *A61C 19/06* | (2006.01) |
| *A61M 5/31* | (2006.01) |
| *A61M 5/315* | (2006.01) |

(52) U.S. Cl.
CPC ............ *A61C 1/088* (2013.01); *A61C 17/028* (2013.01); *A61C 19/063* (2013.01); *A61M 5/3129* (2013.01); *A61M 5/31513* (2013.01); *A61C 2204/002* (2013.01); *A61M 2005/3126* (2013.01); *A61M 2205/583* (2013.01); *A61M 2205/587* (2013.01); *A61M 2205/8206* (2013.01); *A61M 2207/00* (2013.01); *A61M 2210/0631* (2013.01)

(58) Field of Classification Search
CPC ..... A61C 1/088; A61C 17/028; A61C 19/063; A61C 2204/002; A61M 5/3129; A61M 5/31513; A61M 2005/3126; A61M 2205/583; A61M 2205/587; A61M 2205/8206; A61M 2207/00; A61M 2210/0631
USPC .......................................................... 433/29
See application file for complete search history.

(56) References Cited

U.S. PATENT DOCUMENTS

| | | | | |
|---|---|---|---|---|
| 9,428,327 B2 * | 8/2016 | Liu | .......................... | B65D 41/02 |
| 10,195,347 B1 * | 2/2019 | Berkman | ........... | A61M 5/31511 |

| | | | | |
|---|---|---|---|---|
| 2005/0080384 A1 * | 4/2005 | Green | ................ | A61M 5/31511 604/218 |
| 2008/0183122 A1 * | 7/2008 | Fisher | ................ | A61B 17/8836 604/21 |
| 2011/0196312 A1 * | 8/2011 | DeVega | ................ | A61M 5/427 604/218 |
| 2016/0214786 A1 * | 7/2016 | Liu | .................... | A63H 33/3094 |
| 2018/0250103 A1 * | 9/2018 | Pierson | .............. | B05C 17/0103 |

(Continued)

FOREIGN PATENT DOCUMENTS

| | | | | | |
|---|---|---|---|---|---|
| CA | 3124295 A1 * | 6/2020 | ......... | A61C 17/0208 |
| CN | 103654796 A | 3/2014 | | |
| CN | 116920213 A * | 10/2023 | .............. | A61M 5/20 |

(Continued)

*Primary Examiner* — Matthew M Nelson

(74) *Attorney, Agent, or Firm* — The Buche Law Firm, P.C.; Bryce A. Johnson; John K. Buche

(57) ABSTRACT

An illuminated syringe comprising a hollow tubular plunger housing containing a printed circuit board assembly with an LED at its forward tip, a centrally located battery, and an activation switch accessible through a rear access hole in the plunger butt. A translucent cap is ultrasonically welded over the open front end of the plunger housing to seal the PCB and distribute light orthogonally through both the cap and the syringe body. A transparent rubber plunger provides a fluid-tight seal between the housing and a transparent syringe body defining a medicament reservoir, graduated markings, and an expressible tip. When the switch is actuated, the LED projects light through the contained fluid and out the syringe tip, enabling targeted illumination of anatomical sites with limited visibility—particularly oral extraction sockets—while permitting one-handed operation and maintaining disposability of the syringe components.

7 Claims, 6 Drawing Sheets

(56) References Cited

U.S. PATENT DOCUMENTS

2021/0213301 A1 *  7/2021  Akerele-Ale  .....  A61M 5/31571
2021/0298885 A1 *  9/2021  Barrilleaux  ............  A61C 19/08

FOREIGN PATENT DOCUMENTS

JP          2016524991 A  *  8/2016  ............  A61C 19/08
WO      WO 2014117113 A1    7/2013
WO      WO-2015112196 A1 *  7/2015  .............  A61M 5/24

* cited by examiner

1501

SYRINGE AND RELATED METHODS

CROSS-REFERENCE TO RELATED APPLICATIONS

See Application Data Sheet (ADS).

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

This subject matter relates to illuminated medical irrigation and dispensing devices, and more specifically to syringes incorporating integrated LED illumination systems within the plunger assembly for enhanced visibility during the flushing, cleaning, or medication of anatomical sites with limited visibility, such as post-extraction tooth sockets and other oral surgical locations where precise fluid delivery is required.

Listing of the Prior Art

The following references may be to be related to the disclosed subject matter: WO2014117113A1 by Clayton (published Jul. 31, 2013) for a "light for oral anesthesia injection";
  CN103654796A (published Mar. 26, 2014) for a syringe with LED;
  US20050080384A1 by Green, Jr. (published Apr. 14, 2005) for an "illuminating syringe"
  U.S. Pat. No. 9,428,327 by Liu et al (issued Aug. 30, 2016) for a "luminous syringe";
  U.S. Pat. No. 10,195,347 by Berkman et al (issued Feb. 5, 2019) for an "auto-illuminating syringe";
  and, US20110196312A1 by DeVega (published Aug. 11, 2011) for an "illuminated syringe."
  See the Information Disclosure Statements (IDS) of record.

BACKGROUND OF THE INVENTION

Therapeutic irrigation, flushing, and cleaning of oral extraction sites is a critical step in post-operative dental care, particularly after wisdom tooth removal or similar procedures. Patients and clinicians often use syringes to direct saltwater or other sterile irrigating solutions into extraction sockets to remove debris and prevent infection. However, the confined geometry and limited natural light within the oral cavity make it difficult to visualize the extraction site, and improper irrigation can result in retained debris, increased risk of infection or dry socket, and delayed healing. Conventional syringes rely on ambient or external lighting to guide placement and monitor the irrigation process, which may be unavailable, obstructed, or insufficient for ensuring thorough flushing of the socket or surgical region. Similar challenges exist for accurate and hygienic topical delivery of medicaments in such hidden or hard-to-reach regions.

Similarly, Berkman et al. (U.S. Pat. No. 10,195,347) discloses an "auto-illuminating syringe" where a plunger-mounted LED illuminates electrolytic fluids to better view syringe graduations and fluid levels. This system is activated through an electrolytic switch and is optimized for visual contrast in measuring electrolytic solutions, rather than for directly illuminating and irrigating surgical oral sites.

While these prior art solutions provide illumination for syringes used in various settings, they have notable limitations for specialized oral irrigation and cleaning after tooth extraction. DeVega's activation mechanism requires ongoing manual pressure, which may be inconvenient or limit precision during socket irrigation, and the light distribution is not specifically designed to pass through a fluid stream and illuminate the deepest areas of the socket. Berkman's electrolytic system is specific to certain fluid types and circumvents user control of the light source, making it unsuited for controlled, oral-site-specific use. Neither solution provides direct, switch-controlled LED illumination at the plunger tip, passing through both a translucent plug and the flushing or medicating fluid to maximize socket visibility during the irrigation process. Furthermore, ergonomic considerations such as single-handed switch access and the ability to maintain illumination while shifting syringe orientation are not addressed in these references.

Accordingly, a need exists for an improved syringe system that: (1) enables the user to deliver a directed stream of irrigating or medicating fluid while actively illuminating the site of delivery from the tip of the plunger; (2) transmits light through both a translucent plug and the fluid to reach the bottom of extraction sockets or confined spaces; (3) features ergonomic, user-controlled switch placement at the plunger butt for ease of use during home or clinical care; and (4) is optimized not only for medication application but primarily for thorough, visible irrigation and cleaning of post-extraction oral sites to reduce complications and support healing.

SUMMARY OF THE INVENTION

The present disclosure addresses the challenges of visualizing and effectively irrigating oral extraction sites—such as wisdom tooth sockets—by integrating a self-contained LED, circuit board system within a hollow tubular plunger housing. The LED is positioned at the plunger tip behind a translucent cap, with user-friendly switch access provided at the plunger butt. This ergonomic configuration allows precise and controlled illumination directly at the point of fluid delivery, enabling the user to visualize debris and ensure thorough flushing of extraction sockets during oral irrigation procedures. The subject matter described herein pertains to an illuminated syringe system designed to facilitate targeted irrigation—such as flushing extraction sockets with salt water or other oral rinses—within anatomically constrained or low-visibility oral environments, while also being suitable for medication delivery. The device features a hollow tubular plunger housing with an integrated circuit board, a centrally disposed battery, an LED at the tip, a switch accessible at the butt, a translucent cap over the tip, and a translucent rubber plunger for maintaining a fluid-tight seal. Illumination from the LED travels through both the tip and fluid being dispensed, thus enhancing visual feedback and thoroughness of cleaning while flushing or irrigating oral wounds, with the entire assembly fitting into a conventional syringe body. This specialized solution enhances safety, precision, and ease of use in post-surgical dental care as well as in potential medication applications, as illustrated in the accompanying assembly and exploded figures, which detail the LED placement, circuitry, switch accessibility, and sealing mechanisms.

To use the illuminated syringe, ensure the device is fully assembled with the plunger housing, PCB, translucent cap, rubber plunger, and syringe body securely connected. Fill the syringe reservoir with the chosen irrigant (such as salt water) or medication, taking care to avoid air bubbles. Hold the syringe in one hand, locate the access hole at the butt of the plunger, and activate the LED by pressing or switching through the access hole. This illuminates the tip and the fluid within, enhancing visualization of the site to be irrigated or treated. Gently insert the syringe tip into the targeted oral socket, observing the illuminated cavity to guide precise placement. Gradually depress the plunger to deliver the irrigant or medication, watching the illuminated flow as it flushes debris from the socket or treats the area. After completion, release the switch to turn off the LED, then carefully withdraw the tip. Dispose of or sterilize the components as appropriate, according to infection control protocols.

To assemble the illuminated syringe, insert the printed circuit board—with its tip-mounted LED, centrally placed battery, and rear switch—into the hollow tubular plunger housing. Ultrasonically weld the translucent cap over the open end adjacent the LED, allowing effective transmission of light. Insert the translucent rubber plunger so it forms a fluid-tight seal inside the plunger housing. Combine the assembled plunger housing into the butt end of the transparent syringe body, ensuring proper alignment and unrestricted movement, and verify clear visibility of any graduated markings. Confirm that the switch is easily accessed through the plunger butt, and that the syringe tip is securely attached at the reservoir end. Perform a functional test by actuating the switch to ensure the LED illuminates correctly through the tip and fluid, readying the device for sterile oral irrigation or medication delivery.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which.

In the figures, the following components of the preferred embodiment are shown in connection with the corresponding reference numeral identified below.

Overall Assembly

1000—Illuminated Syringe

Tubular Plunger Housing Assembly

1100—Tubular Plunger Housing

1110—Open End (of tubular plunger housing)

1120—Butt (of tubular plunger housing)

Figure 1:
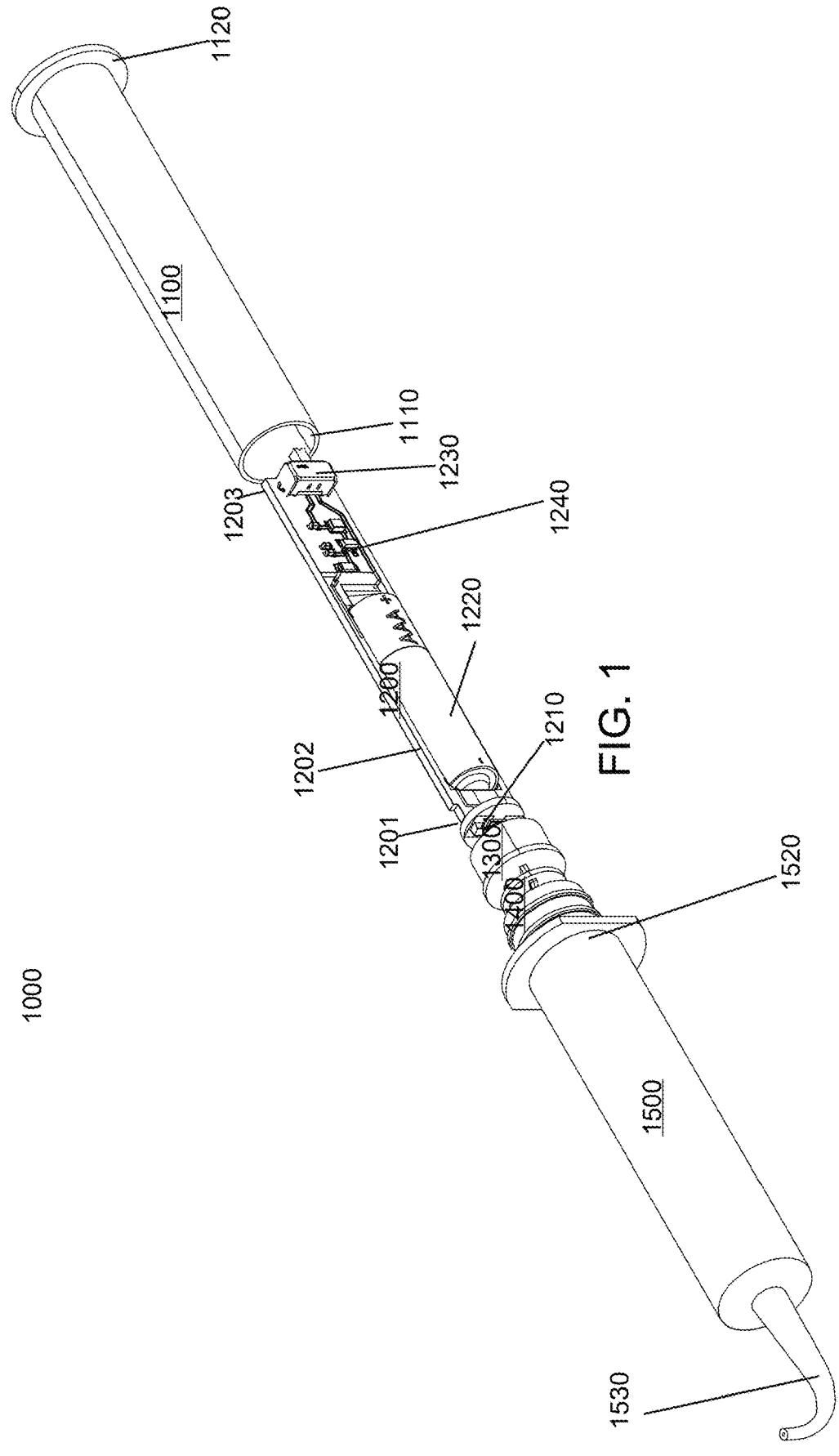
FIG. 1 is an perspective exploded view of the syringe 1000 showing: (1) the tubular plunger housing 1100 with an open end 1110 and butt 1120 with an access hole 1121 for exposing a switch of a PCB 1200 housed within the tubular plunger housing 1100; (2) the PCB 1200 with LED 1210 on its tip 1201, a Battery 1220 disposed within a slot 1202 of the PCB 1200, a switch 1230 on a rear end 1203 of the PCB 1200, and circuitry 1240 connecting the LED 1210, the battery 1220, and the switch 1230 of the PCB 1200; (3) a transparent or translucent cap 1300 or lamp cover 1300 that is ultrasonically welded over the open end 1110 of the tubular plunger housing 1100 to close the open end 1110 and where the cap/cover 1300 is located adjacent the LED 1210 of the PCB 1200 so that light from the LED can be distributed orthogonally from the tip 1201 of the PCB 1200; (4) a transparent or translucent rubber plunger 1400 for providing a fluid-tight seal between the tubular plunger housing 1100 and a syringe body 1500; and (5) the translucent or transparent syringe body 1500 defining a reservoir 1510 for receiving a medication or irrigant and a butt end 1520 for receiving the plunger 1400 and tubular plunger housing 1100, and a syringe tip 1530 that is adapted for expressing the medication or irrigant from the reservoir 1510 whenever the plunger is pushed further into the syringe body 1500 by pump action operation.

1121—Access Hole (in butt for exposing switch)

Printed Circuit Board (PCB) Assembly

1200—PCB (Printed Circuit Board)

1201—Tip (of PCB)

1202—Slot (in PCB for battery)

1203—Rear End (of PCB)

1210—LED (Light Emitting Diode)

1220—Battery

1230—Switch

1240—Circuitry (connecting LED, battery, and switch)

Cap/Lamp Cover Assembly

1300—Transparent or Translucent Cap/Lamp Cover

Plunger Sealing Assembly

1400—Transparent or Translucent Rubber Plunger

Syringe Body Assembly

1500—Translucent or Transparent Syringe Body

1501—Graduations (for measuring fluid amount)

1510—Reservoir (for receiving medication or irrigant)

1520—Butt End (of syringe body for receiving plunger)

1530—Syringe Tip (for expressing medication or irrigant)

Assembly Notes

The cap 1300 may be ultrasonically welded over the open end 1110 of the tubular plunger housing 1100.

The cap 1300 may be positioned adjacent to the LED 1210 for orthogonal light distribution.

The rubber plunger 1400 might provide fluid-tight seal between tubular plunger housing 1100 and syringe body 1500.

The switch 1230 may be accessible through access hole 1121 in the butt 1120 of the tubular plunger housing 1100.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

This is a specification of an illuminated syringe system specifically designed to facilitate accurate medication or irrigant delivery to hard-to-see anatomical locations, particularly oral extraction sockets following dental surgery. The invention integrates a self-contained LED illumination system directly within the syringe plunger to provide targeted lighting through the medication or irrigant and syringe tip, enabling precise application even in low-light conditions or confined oral spaces. The details of the disclosed subject matter are described with reference to the drawings.

FIGS. 1 through 3B illustrate an exploded syringe 1000. As shown, the illuminated syringe 1000 comprises five primary components working in coordination to provide both medication or irrigant delivery and targeted illumination. Specifically, the five components could be: (1) Tubular Plunger Housing (1100); Printed Circuit Board Assembly (1200)I; Transparent/Translucent Cap (1300); Sealing Plunger (1400); and Syringe Body (1500).

FIGS. 4 through 7 illustrate a syringe 1000 with a depressed plunger housing 1100. The plunger operates in a typical manner where a reservoir is filled with medication or irrigant and dispensed through the syringe tip. The plunger may be depressed to evacuate the contents of the reservoir. The plunger housing may be withdraw to fill the reservoir as the tip is submerged in a fluid medication or irrigant. As discussed in greater detail the syringe is illuminated.

Figures 8, 9, 10, 11, 12, 13, 14:
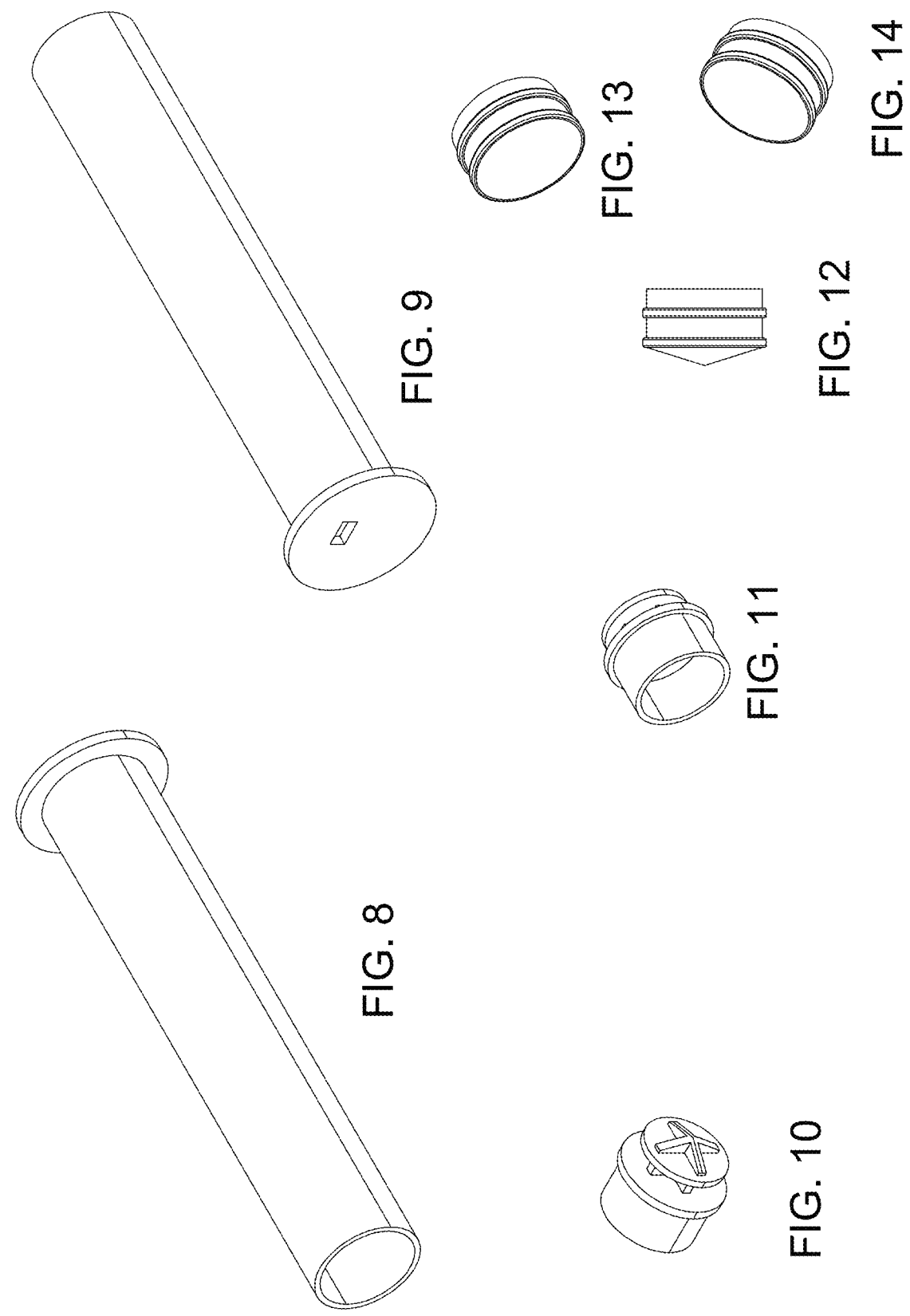
FIG. 8 is a front perspective view of the plunger housing 1100.
FIG. 9 is a back perspective view of the plunger housing 1100.
FIG. 10 is a front perspective view of the cap 1300.
FIG. 11 is a back perspective view of the cap 1300.
FIG. 12 is a side view of the plunger 1400.
FIG. 13 is a front perspective view of the plunger 1400.
FIG. 14 is another front perspective view of the plunger 1400.
Figures 15, 16, 17, 18, 19:
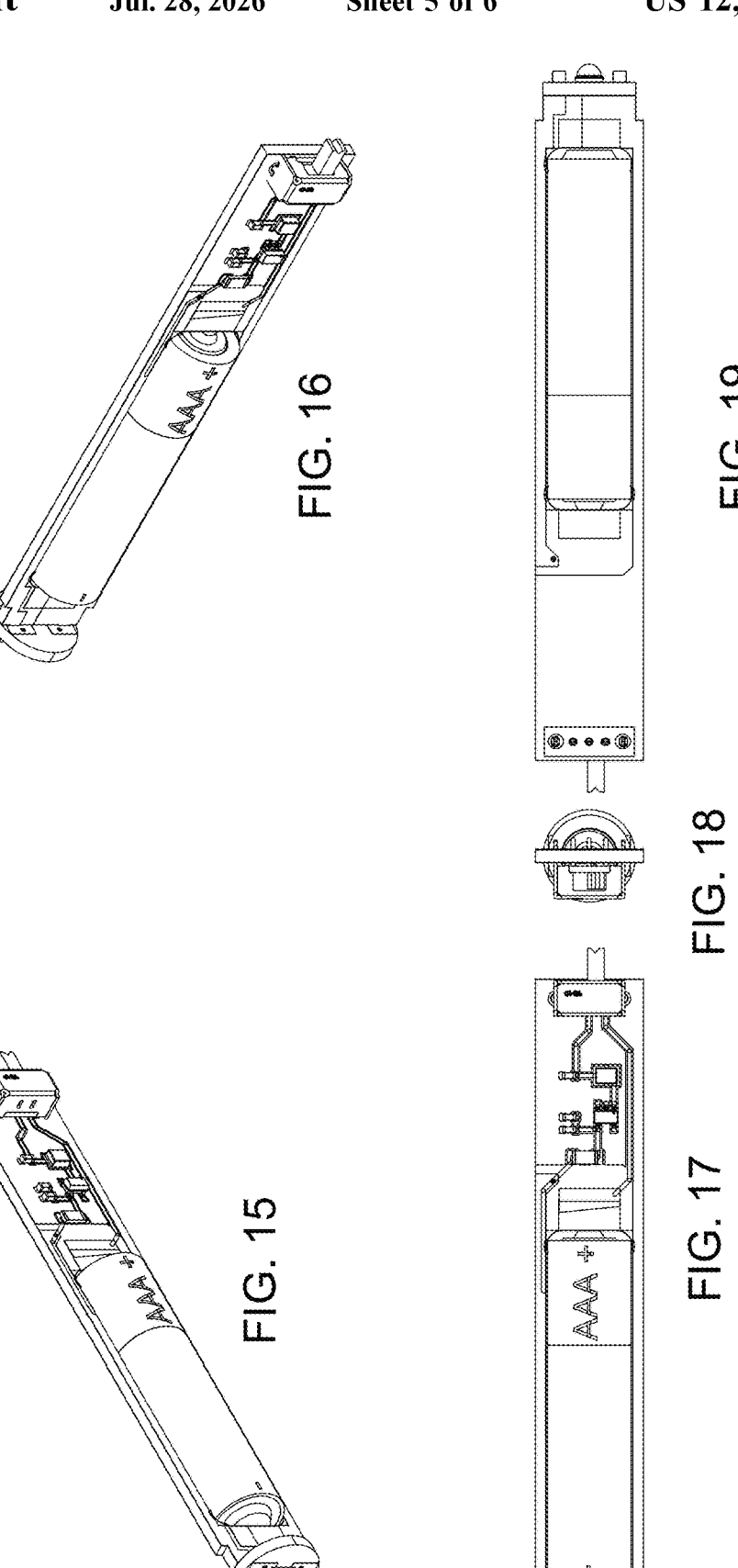
FIG. 15 is a perspective view of the PCB 1200.
FIG. 16 is another perspective view of the PCB 1200.
FIG. 17 is a side view of the PCB 1200.
FIG. 18 is a rear view of the PCB 1200 showing the switch 1230.
FIG. 19 is another side view of the PCB 1200.

A preferred embodiment of the Tubular Plunger Housing (1100) is best illustrated in FIGS. 8 and 9. As shown the housing may be a hollow cylindrical housing featuring an open end 1110 for LED light transmission and a butt end 1120 with an access hole 1121 that exposes the activation switch. This housing serves as the structural foundation for the internal electronics while maintaining the mechanical functionality of a traditional syringe plunger.

A preferred embodiment of the Printed Circuit Board Assembly (1200) is shown in FIGS. 15 through 19. As shown, the core of the syringe may include the PCB 1200 that fits entirely within the tubular plunger housing 1100. The PCB of the preferred embodiment features an LED 1210 positioned at its tip 1201 for optimal light projection, a centrally-disposed battery 1220 housed within a dedicated slot 1202, and an activation switch 1230 located at the rear end 1203. Connecting circuitry 1240 electrically links these components to create a self-contained illumination system.

Figures 2, 3A, 3B:
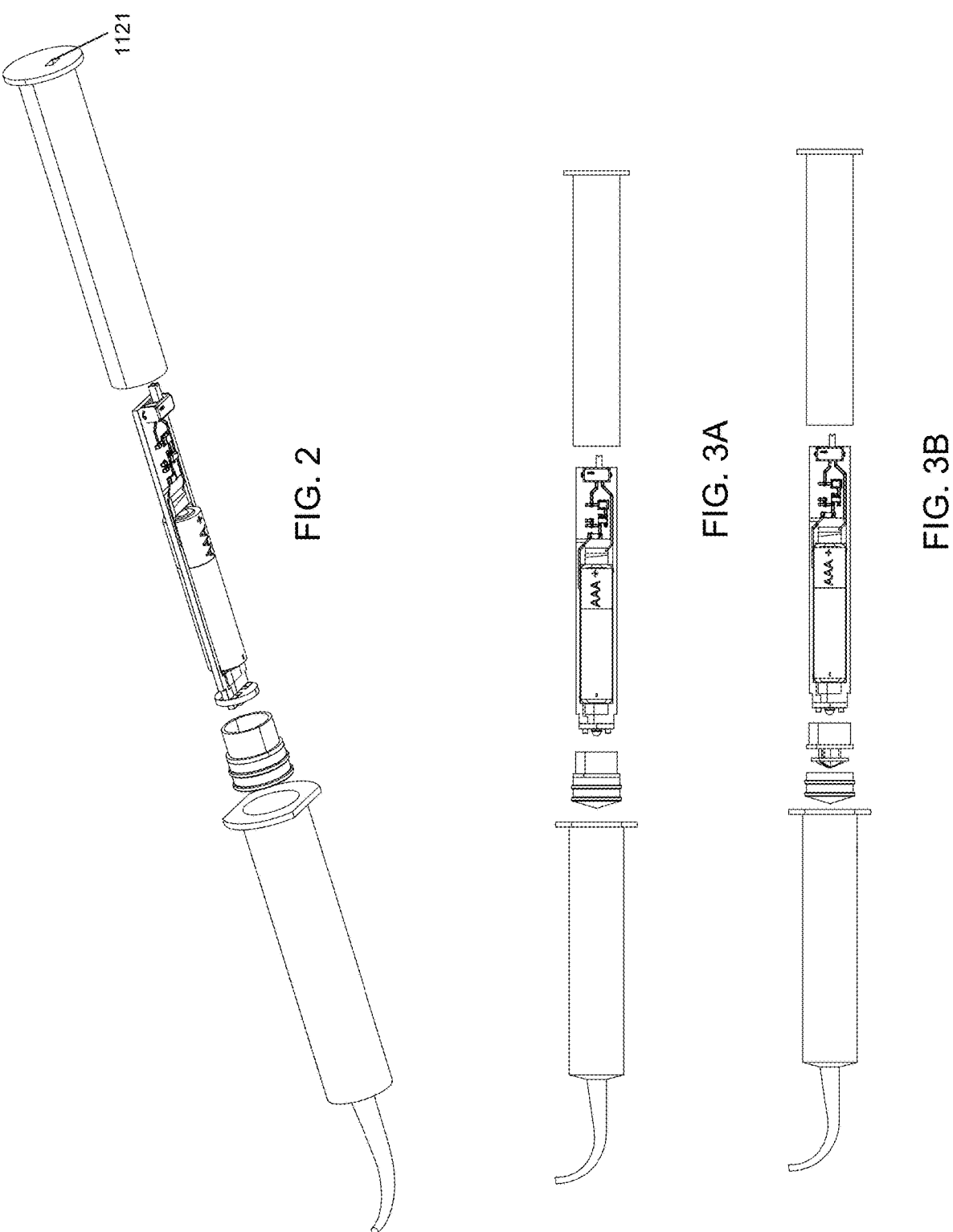
FIG. 2 is another exploded perspective view of the syringe 1000.
FIG. 3A is an exploded side view of the syringe 1000 with the cap 1300 and plunger 1400 coupled or assembled.
FIG. 3B is an exploded side view of the syringe 1000 with the cap 1300 and plunger decoupled or disassembled.
Figure 7:
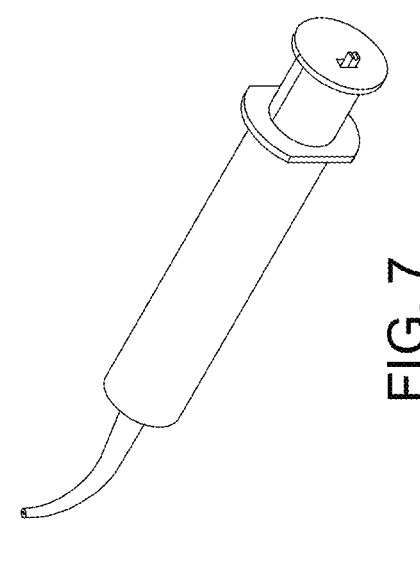
FIG. 7 is another perspective view of the assembled syringe 1000 with the plunger housing 1100 in a fully depressed state.
Figure 6:
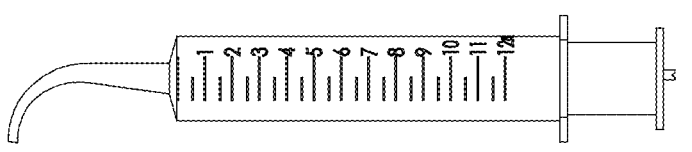
FIG. 6 is another side view of the assembled syringe with the plunger housing 1100 in a fully depressed state showing graduations 1501 for measuring the amount of fluid in the syringe 1000 reservoir 1510.
Figure 5:
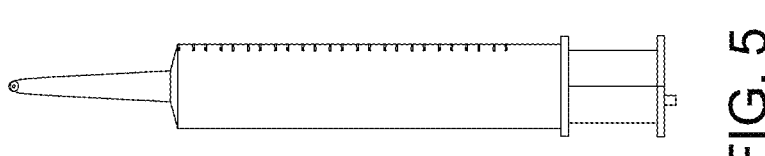
FIG. 5 is a side view of the assembled syringe with the plunger housing 1100 in a fully depressed state.
Figure 4:
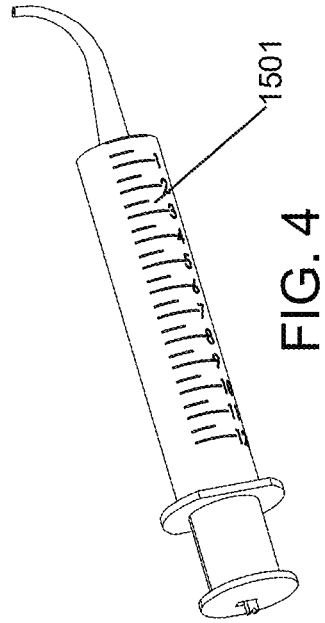
FIG. 4 is a perspective view of the assembled syringe with the plunger housing 1100 in a fully depressed state.

A preferred embodiment of a Transparent/Translucent Cap (1300) is shown in FIGS. 10 and 11. As shown, the preferred lamp cover 1300 may be ultrasonically welded over the open end 1110 of the tubular plunger housing to create a sealed yet light-transmissive barrier. The cap is strategically positioned adjacent to the LED 1210 to enable orthogonal light distribution from the PCB tip 1201, ensuring maximum illumination efficiency. The cap 1300 preferably seals the PCB 1200 within the tubular housing 1100 so that it cannot be damaged e.g. by contact with medication or irrigant from within the syringe 1000. FIGS. 3A and 3B show how the cap 1300 is associated with the plunger 1400 discussed later. Suitably, the cap 1300 may be defined by a light conductive material such that the light source may be transmitted through the various surfaces of the cap, including any fins or digits. Several light-conductive materials include optical fibers (such as silica or plastic optical fibers), acrylic (PMMA), polycarbonate, glass, and certain translucent plastics like polycarbonate, polyethylene, and acrylics used for light guides and light pipes. A non-limiting list includes: Polymethyl Methacrylate (PMMA/Acrylic); Polycarbonate (PC); TOPAS Cyclic Olefin Copolymer (COC); Ultraviolet Transmitting (UVT) Acrylic; High-Purity Silica Glass (optical fiber cores); Plastic Optical Fibers (POF).

FIGS. 12 through 14 illustrate a preferred embodiment of a Sealing Plunger (1400). As shown, a transparent or translucent rubber plunger 1400 may provide the essential fluid-tight seal between the tubular plunger housing 1100 and the syringe body 1500, maintaining sterility and preventing medication or irrigant leakage while allowing light transmission. FIGS. 3A and 3B show how the cap 1300 is associated with the plunger 1400.

Figures 20, 21, 22:
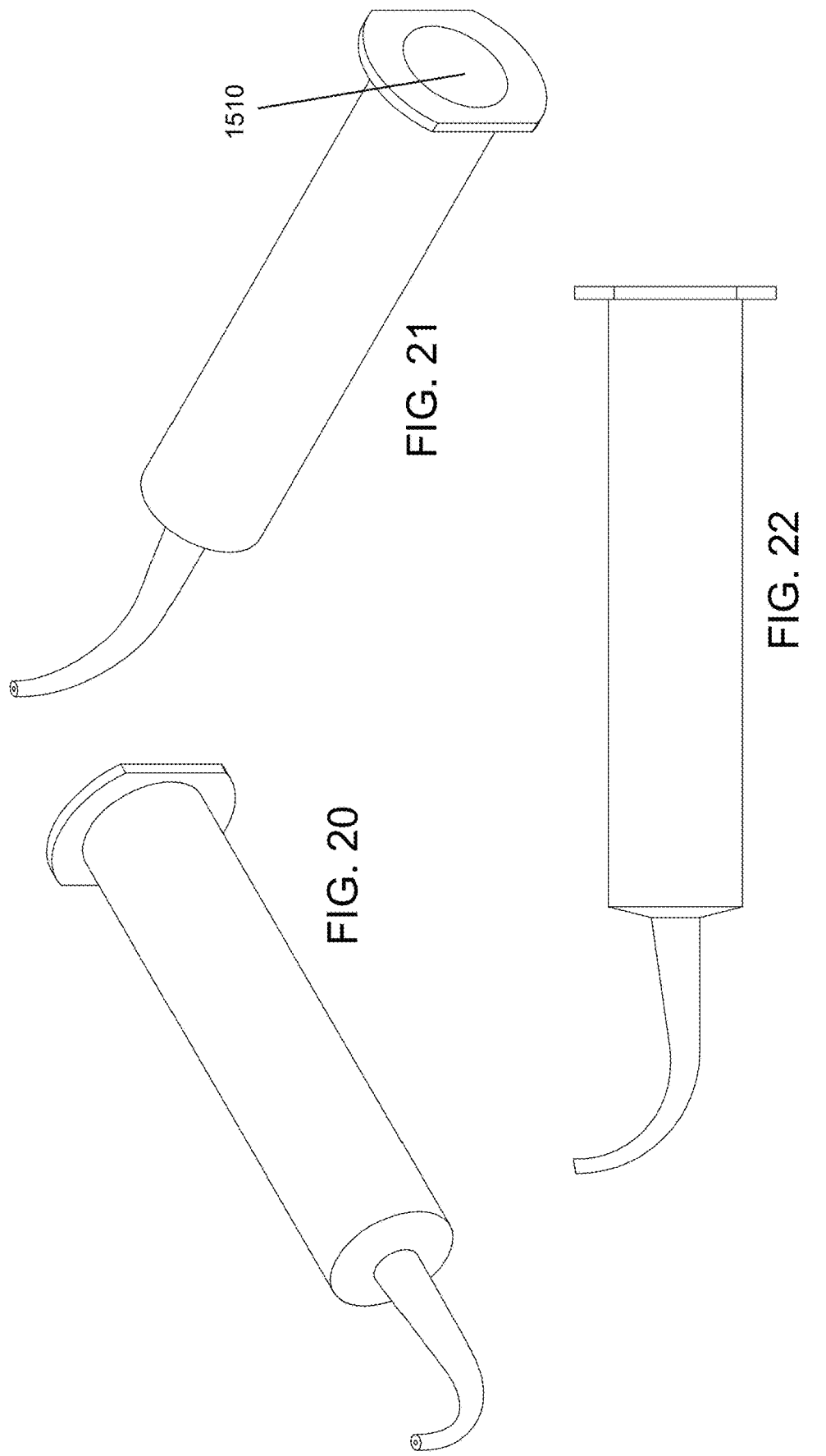
FIG. 20 is a front perspective view of the syringe housing 1500.
FIG. 21 is a rear perspective view of the syringe housing 1500.
FIG. 22 is a side view of the syringe housing 1500.

FIGS. 20 through 22 illustrate a preferred embodiment of a Syringe Body (1500). As shown, a translucent or transparent syringe body 1500 defining a medication or irrigant reservoir 1510, a butt end 1520 for receiving the plunger assembly, and a dispensing tip 1530. The transparent construction allows the internal LED illumination to pass through the contained medication or irrigant and illuminate the target application site. Graduated markings 1501 enable precise medication or irrigant measurement. The tip may be curved e.g., to promote delivery of a medication or irrigant to a sore. Suitably, the syringe body 1500 may be defined by a light conductive material such that the light source may be transmitted through the various surfaces of the body, especially at the tip and adjacent surfaces.

The preferred embodiment of the syringe 1000 operates through a simple yet effective mechanism: when the switch 1230 is activated through the access hole 1121 at the butt of the plunger housing, the LED 1210 illuminates and projects light through the transparent cap 1300, through the medication or irrigant in reservoir 1510, and out through the syringe tip 1530. This creates a targeted beam of light that illuminates the application site, such as a tooth extraction socket, enabling the user to accurately position the syringe and dispense medication or irrigant with improved visibility.

Suitably, this integrated approach provides several key advantages over existing illuminated syringe designs: the LED is positioned optimally within the plunger for direct light transmission through the medication or irrigant; the switch is ergonomically accessible for one-handed operation during delicate procedures; the entire system is self-contained within the disposable syringe; and the design specifically addresses the challenges of oral medication or irrigant delivery where external lighting is insufficient or impractical.

Example 1: Method of Using the Illuminated Syringe

To prepare the syringe 1000, a user may begin by assembling the illuminated syringe 1000 by ensuring the PCB 1200 with LED 1210, battery 1220, and switch 1230 is properly housed within the tubular plunger housing 1100, and that the translucent cap 1300 is securely welded over the open end 1110. Next a user may attach the transparent rubber plunger 1400 to create a fluid-tight seal, then insert the assembled plunger housing into the butt end 1520 of the transparent syringe body 1500. Finally, a user may fill the reservoir 1510 with the prescribed medication or irrigant by drawing the plunger back to create suction and allowing the medication or irrigant to enter through the syringe tip 1530, using the graduated markings 1501 to measure the exact dosage required. Pre-Application Setup: Position yourself comfortably with adequate access to the patient's oral cavity, ensuring the extraction socket or target anatomical site is accessible. Hold the syringe 1000 with your dominant hand, gripping the syringe body 1500 while keeping your thumb positioned near the access hole 1121 at the butt 1120 of the tubular plunger housing for easy switch activation. Verify that the medication or irrigant level in the reservoir 1510 corresponds to the prescribed dosage using the graduated markings 1501 visible through the transparent syringe body.

To illuminate the syringe, before inserting the syringe tip 1530 into the oral cavity, a user may activate the illumination system by pressing the switch 1230 through the access hole 1121 at the butt 1120 of the plunger housing. Suitably, this action energizes the LED 1210 at the tip 1201 of the PCB 1200, causing light to emit through the translucent cap 1300 and illuminate the medication or irrigant within the reservoir 1510. In one version, the light travels through the transparent syringe body 1500 and projects from the syringe tip 1530, creating a targeted illumination that will highlight the application site.

To provide precise application, a user, with the LED illuminated, may carefully position the syringe tip 1530 near the target extraction socket or anatomical site, using the projected light to clearly visualize the precise location for medication or irrigant delivery. The illumination passes through both the contained medication or irrigant and the transparent syringe components, providing direct lighting of the application area that was previously difficult or impossible to see clearly. Next, a user may slowly advance the plunger housing 1100 deeper into the syringe body 1500 using controlled pump action to express the medication or irrigant from the reservoir 1510 through the tip 1530 directly onto the illuminated target site.

To accomplish controlled dispensing, a user may continue the pump action while maintaining switch activation to keep the application site illuminated throughout the entire medication or irrigant delivery process. The combination of targeted lighting and precise plunger control allows for accurate placement of the medication or irrigant exactly where needed, minimizing waste and ensuring therapeutic effectiveness. Next a user may monitor the medication or irrigant level through the transparent syringe body 1500 using the graduated markings 1501 to confirm complete delivery of the prescribed dosage.

For a user to accomplish completion and deactivation, the user may, once the prescribed amount of medication or irrigant has been delivered to the extraction socket or target site, release the switch 1230 to deactivate the LED 1210 and conserve battery 1220 power. Next, the user may carefully withdraw the syringe tip 1530 from the oral cavity. In one mode of operation, the entire procedure can be performed with one-handed operation, leaving the other hand free to assist with patient positioning or oral cavity access as needed, while the self-contained illumination system eliminates the need for external lighting sources during the critical medication or irrigant application phase.

Example 2: Method of Assembling the Illuminated Syringe

A user may accomplish PCB Installation and Testing by first verifying that the PCB 1200 is properly configured with the LED 1210 positioned at the tip 1201, the battery 1220 securely seated within the slot 1202, and the switch 1230 accessible at the rear end 1203 of the PCB. Next, the user may ensure all circuitry 1240 connections between the LED, battery, and switch are complete and functional by briefly testing the switch to confirm LED illumination before proceeding with housing installation. After that, the user may Insert the fully assembled PCB 1200 into the hollow tubular plunger housing 1100 through the open end 1110, carefully positioning the circuit board so that the LED 1210 at the tip 1201 is oriented toward the open end while the switch 1230 at the rear end 1203 aligns with the access hole 1121 in the butt 1120 of the housing.

A user may accomplish cap sealing and LED positioning via positioning the transparent or translucent cap 1300 over the open end 1110 of the tubular plunger housing 1100, ensuring that the cap is properly aligned adjacent to the LED 1210 to enable optimal orthogonal light distribution from the PCB tip 1201. Next, the user may apply ultrasonic welding to permanently bond the cap 1300 to the open end 1110 of the plunger housing, creating a sealed enclosure that protects the internal electronics while maintaining light transmission capability. At some point, the user may verify that the welded seal is complete and that the LED 1210 remains properly positioned behind the translucent cap for maximum illumination efficiency through the cap material.

A user may ensure plunger seal integration via attaching the transparent or translucent rubber plunger 1400 to the exterior of the tubular plunger housing 1100 and ensuring that the plunger creates a proper fluid-tight seal that will prevent medication or irrigant leakage when inserted into the syringe body 1500. The rubber plunger 1400 can be positioned to provide both sealing functionality and light transmission capability, allowing illumination from the internal LED 1210 to pass through both the cap 1300 and the plunger material. Next a user may test the seal integrity by applying gentle pressure to confirm that the rubber plunger 1400 maintains proper contact with the plunger housing 1100 without compromising the access hole 1121 that exposes the switch 1230.

A user may perform syringe body preparation and final assembly via preparing the translucent or transparent syringe body 1500, ensuring the reservoir 1510 is clean and free of debris, and that the graduated markings 1501 are clearly visible for accurate medication or irrigant measurement. Next, a user may insert the assembled plunger housing unit (comprising the tubular plunger housing 1100, sealed cap 1300, and attached rubber plunger 1400) into the butt end 1520 of the syringe body 1500, ensuring proper alignment and seating of the rubber plunger within the body. Finally, a user may verify that the plunger housing can move smoothly within the syringe body to enable proper pump action while maintaining the fluid-tight seal necessary for medication or irrigant dispensing through the syringe tip 1530.

Last, a user may perform functional testing and quality verification. First, a user may conduct a comprehensive functional test of the assembled illuminated syringe 1000 by actuating the switch 1230 through the access hole 1121 to verify that the LED 1210 illuminates properly and that light projects effectively through the cap 1300, through the transparent syringe body 1500, and would emit from the syringe tip 1530 during use. Next the user can test the mechanical operation by performing pump action with the plunger housing 1100 to ensure smooth movement within the syringe body 1500 and proper seal maintenance by the rubber plunger 1400. Finally, a user may verify that the graduated markings 1501 remain visible through the transparent syringe body and that the overall assembly maintains structural integrity while preserving both illumination and dispensing functionality for safe and effective medical use.

The disclosed syringe 1000 thus solves the fundamental problem of accurate medication or irrigant delivery to poorly-visible anatomical sites by integrating illumination directly into the dispensing mechanism, improving patient outcomes and reducing the complexity of post-surgical care procedures.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus, the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

I claim:

1. An illuminated syringe comprising:
   (1) a hollow tubular plunger housing having an open end with a circular opening and a butt end;
   (2) a printed circuit board disposed within said hollow tubular plunger housing, said printed circuit board comprising an LED positioned at the open end of the plunger housing;
   (3) a battery that is disposed at a central location within the tubular plunger housing, said battery being cylindrical and disposed coaxially relative to the circular opening;
   (4) an on/off mechanism disposed on the printed circuit board and accessible outside of the tubular plunger housing;
   (5) circuitry electrically connecting said LED, said battery, and said on/off mechanism;
   (6) a translucent cap that has at least one light conductive digit or fin sealed over said open end of said hollow tubular plunger housing and positioned adjacent to said LED such that light emitting from the LED is transmitted through at least one surface of the digit or fin;
   (7) a translucent rubber plunger within which said digit or fin is disposed, the translucent rubber plunger providing a fluid-tight seal with said hollow tubular plunger housing; and
   (8) a transparent syringe body defining a reservoir for receiving medication or irrigant, a butt end for receiving said hollow tubular plunger housing, and a syringe tip for expressing said medication or irrigant.

2. The illuminated syringe of claim 1, wherein said LED is on a circular disk that is coaxially disposed in and relative to the circular opening and said translucent cap that is partially disposed within the circular opening, made of a light-conductive material, and secured to said open end of said hollow tubular plunger housing.

3. The illuminated syringe of claim 2, wherein said transparent syringe body includes graduated markings for measuring medication or irrigant volume within said reservoir.

4. The illuminated syringe of claim 2, wherein;

said at least one surface of the digit or fin is orthogonal relative to a coaxis of the tubular plunger housing and the translucent cap; and, said LED is positioned to project light through said translucent cap via transmission of light through the at least one surface of said digit or fin and through said medication or irrigant in said reservoir.

5. The illuminated syringe of claim 4, wherein said battery is centrally disposed within a slot formed in said printed circuit board.

6. The illuminated syringe of claim 5, wherein said tubular housing features an access hole and said on/off mechanism is actuatable through said access hole to selectively illuminate said LED.

7. The illuminated syringe of claim 6, wherein said syringe tip is adapted for delivering medication or irrigant to oral extraction sockets.

\*   \*   \*   \*   \*